United States Patent [19]
MacLaren et al.

[11] Patent Number: 6,039,974
[45] Date of Patent: Mar. 21, 2000

[54] PHARMACEUTICAL COMPOSITION FOR COMBINATION OF PIPERIDINOALKANOL-DECONGESTANT

[75] Inventors: David D. MacLaren; John R. Lefler, both of Overland Park, Kans.; Sharon K. Minish, Independence, Mo.

[73] Assignee: Hoechst Marion Roussel, Inc., Bridgewater, N.J.

[21] Appl. No.: 09/127,478

[22] Filed: Jul. 31, 1998

Related U.S. Application Data

[60] Provisional application No. 60/090,105, Aug. 26, 1997.

[51] Int. Cl.⁷ .............................. A61K 9/22; A61K 9/24; A61K 9/28
[52] U.S. Cl. ................ 424/472; 424/468; 424/474; 424/475; 514/770; 514/778; 514/781; 514/783; 514/784; 514/853
[58] Field of Search ...................... 424/472, 473, 424/468, 474, 475, 480, 482

[56] References Cited

U.S. PATENT DOCUMENTS

| | | | |
|---|---|---|---|
| 3,806,526 | 4/1974 | Carr et al. | 260/293.64 |
| 3,878,217 | 4/1975 | Carr et al. | 260/293.64 |
| 3,966,949 | 6/1976 | Webb | 424/250 |
| 3,979,520 | 9/1976 | Rothe et al. | 424/321 |
| 4,060,634 | 11/1977 | Rothe et al. | 424/321 |
| 4,196,188 | 4/1980 | Besins | 424/37 |
| 4,254,129 | 3/1981 | Carr et al. | 424/267 |
| 4,254,130 | 3/1981 | Carr et al. | 424/267 |
| 4,285,957 | 8/1981 | Carr et al. | 424/267 |
| 4,285,958 | 8/1981 | Carr et al. | 424/267 |
| 4,609,675 | 9/1986 | Franz | 514/568 |
| 4,639,458 | 1/1987 | Katdare | 424/15 |
| 4,840,799 | 6/1989 | Appelgren et al. | 424/493 |
| 4,916,163 | 4/1990 | Ni | 514/593 |
| 4,929,605 | 5/1990 | Domet et al. | 514/54 |
| 4,963,540 | 10/1990 | Maxson et al. | 514/177 |
| 4,996,061 | 2/1991 | Webb et al. | 424/475 |
| 4,999,226 | 3/1991 | Schock et al. | 424/472 |
| 5,021,242 | 6/1991 | Romer et al. | 424/436 |
| 5,049,568 | 9/1991 | Kristof et al. | 514/317 |
| 5,169,638 | 12/1992 | Dennis et al. | 424/457 |
| 5,271,944 | 12/1993 | Lee | 424/489 |
| 5,375,693 | 12/1994 | Woosley et al. | 514/317 |
| 5,376,386 | 12/1994 | Ganderton et al. | 424/499 |
| 5,429,825 | 7/1995 | Reo et al. | 424/490 |
| 5,451,409 | 9/1995 | Rencher et al. | 424/468 |
| 5,458,879 | 10/1995 | Singh et al. | 424/400 |
| 5,472,704 | 12/1995 | Santus et al. | 424/435 |
| 5,474,757 | 12/1995 | Yang | 514/562 |
| 5,476,654 | 12/1995 | Conte et al. | 424/78.08 |
| 5,487,901 | 1/1996 | Conte et al. | 424/472 |
| 5,516,803 | 5/1996 | Raffa | 514/570 |
| 5,541,210 | 7/1996 | Cupps et al. | 514/394 |
| 5,567,439 | 10/1996 | Myers et al. | 424/486 |
| 5,574,045 | 11/1996 | Ortyl et al. | 514/317 |
| 5,587,172 | 12/1996 | Cherukuri et al. | 424/401 |
| 5,691,370 | 11/1997 | Cupps et al. | 514/394 |
| 5,738,872 | 4/1998 | Ortyl et al. | 424/452 |
| 5,837,379 | 11/1998 | Chen et al. | 424/465 |
| 5,855,912 | 1/1999 | Ortyl et al. | 424/452 |
| 5,869,479 | 2/1999 | Kreutner et al. | 514/212 |
| 5,876,759 | 3/1999 | Gowan | 424/494 |

FOREIGN PATENT DOCUMENTS

| | | |
|---|---|---|
| 2237450 | 11/1998 | Canada . |
| 0111114 | 10/1983 | European Pat. Off. . |
| 0173293 | 8/1985 | European Pat. Off. . |
| 0260241 | 3/1988 | European Pat. Off. . |
| 0310999 | 4/1989 | European Pat. Off. . |
| 0311067 | 4/1989 | European Pat. Off. . |

(List continued on next page.)

OTHER PUBLICATIONS

Comprehensive Medicinal Chemistry, vol. 5, Biopharmaceutics, pp. 563–566, 1990.
Chemical Abstracts, vol. 129, No. 3, Jul. 20, 1998, Abstract No. 32342.
Asgharnejad et al, Chemical Abstracts, vol. 126, #347314, 1997.
Rijksuniversiteit, Chemical Abstracts, vol. 106, #90173, 1987.
Schock et al, Chemical Abstracts, vol. 113, #46295, 1990.

*Primary Examiner*—James M. Spear
*Attorney, Agent, or Firm*—Charlotte L. Barney

[57] ABSTRACT

The present invention provides a pharmaceutical composition in the form of a bilayer tablet comprising, (a) a first discrete zone made with Formulation (A) which comprises, a therapeutically effective decongestant amount of a sympathomimetic drug, or a pharmaceutically acceptable salt thereof, in an amount of about 18% to about 39% by weight of Formulation (A), and a first carrier base material, the first carrier base material comprising a mixture of;
  (I) carnauba wax in an amount of about 59% to about 81% by weight of Formulation (A); and
  (ii) a suitable antiadherent in an amount of about 0.25% to about 2.00% by weight of Formulation (A);

wherein said first carrier base material provides a sustained release of the sympathomimetic drug; and (b) a second discrete zone made with Formulation (B) which comprises a therapeutically effective antihistaminic amount of a piperidinoalkanol, or a pharmaceutically acceptable salt thereof, in an amount of about 15% to about 30% by weight of Formulation (B) and a second carrier base material, the second carrier base comprising a mixture of;
  (I) a cellulose diluent in an amount of about 27% to about 73% by weight of Formulation (B);
  (ii) pregelatinized starch in an amount of about 15% to about 30% by weight of Formulation (B);
  (iii) a suitable disintegrant in an amount of about 0.25% to about 6.00% by weight of Formulation (B); and
  (iv) a suitable lubricant in an amount of about 0.25% to about 2.00% by weight of Formulation (B);

wherein said second carrier base material provides an immediate release of the piperidinoalkanol or the pharmaceutically acceptable salt thereof.

13 Claims, No Drawings

FOREIGN PATENT DOCUMENTS

| | | |
|---|---|---|
| 0348683 | 1/1990 | European Pat. Off. . |
| 0396404 | 11/1990 | European Pat. Off. . |
| 0468392 | 1/1992 | European Pat. Off. . |
| 0508969 | 10/1992 | European Pat. Off. . |
| 0582380 | 2/1994 | European Pat. Off. . |
| 0380023 | 3/1994 | European Pat. Off. . |
| 0636364 | 2/1995 | European Pat. Off. . |
| 0636365 | 2/1995 | European Pat. Off. . |
| 0639976 | 9/1998 | European Pat. Off. . |
| 8707502 | 12/1987 | WIPO . |
| 9311744 | 6/1993 | WIPO . |
| 9317665 | 9/1993 | WIPO . |
| 9323047 | 11/1993 | WIPO . |
| 9403170 | 2/1994 | WIPO . |
| 9409761 | 5/1994 | WIPO . |
| 9413271 | 6/1994 | WIPO . |
| 9500482 | 1/1995 | WIPO . |
| 9501781 | 1/1995 | WIPO . |
| 9510278 | 4/1995 | WIPO . |
| 9523591 | 9/1995 | WIPO . |
| 9531437 | 11/1995 | WIPO . |
| 9626726 | 9/1996 | WIPO . |
| 9639139 | 12/1996 | WIPO . |
| 9806394 | 2/1998 | WIPO . |
| 9833489 | 8/1998 | WIPO . |
| 9847535 | 10/1998 | WIPO . |
| 9848839 | 11/1998 | WIPO . |
| 9907342 | 2/1999 | WIPO . |
| 9908690 | 2/1999 | WIPO . |

PHARMACEUTICAL COMPOSITION FOR COMBINATION OF PIPERIDINOALKANOL-DECONGESTANT

This application claims the priority of U.S. Provisional Application Ser. No. 60/090,105, filed Aug. 26, 1997, abandoned.

BACKGROUND OF THE INVENTION

It has been established that various piperidinoalkanol compounds are useful as antihistamines, antiallergy agents and bronchodilators as disclosed in U.S. Pat. Nos. 3,878,217, 4,254,129 and 4,285,957. Several examples of formulations of these various piperidinoalkanol compounds are described below.

J. Domet and D. Shah describe in U.S. Pat. No. 4,929,605, a pharmaceutical composition in solid unit dosage form, comprising, a therapeutically effective amount of a piperidinoalkanol compound, or a pharmaceutically acceptable salt thereof, a pharmaceutically acceptable nonionic or cationic surfactant in an amount of from about 0.1% to about 6% by weight of the composition, and a pharmaceutically acceptable carbonate salt in an amount of from about 2% to about 50% by weight of the composition.

N. Webb and G. Hammer describe in U.S. Pat. No. 4,996,061, a pharmaceutical composition in the form of a multiple-compression tablet comprising a discrete zone made from a formulation which provides sustained-release of a therapeutically effective decongestant amount of a sympathomimetic drug and a discrete zone made from a different formulation which provides immediate release of a therapeutically effective antihistaminic amount of a piperidinoalkanol and, optionally, a therapeutically effective decongestant amount of a sympathomimetic drug.

H. Schock, et al. describe in U.S. Pat. No. 4,999,226 a multi-layered tablet containing an ibuprofen layer, a piperidinoalkanol antihistamine layer, and a layer or layers containing conventional pharmaceutical excipients which is interspersed between the ibuprofen and piperidinoalkanol layer and serves to physically separate them. It was disclosed by Schock et al. that attempts to formulate a two-layered tablet failed as a result of chemical degradation of the piperidinoalkanol in the presence of ibuprofen. In addition, attempts to retard this rate of degradation using anti-oxidants also failed.

T. Ortyl, et al. disclose in International Application No. WO 96/26726, published Sep. 6, 1996, a pharmaceutical composition in solid unit dosage form comprising a piperidinoalkanol compound and at least one inert ingredient.

A number of products are currently available for the treatment of the symptomatology associated with ailments such as the common cold, seasonal rhinitis, sinus headaches, sinusitis, etc., which contain multiple therapeutic agents. Many of these products contain an antihistamine in combination with a sympathomimetic decongestant. Such combination products are convenient for the patient since they allow the patient to obtain relief from numerous symptoms without taking multiple medications.

An attempt was made to formulate a multiple-compression tablet containing the sympathomimetic drug, pseudoephedrine hydrochloride in sustained release form with the piperidinoalkanol, 4-[4-[4-(hydroxydiphenylmethyl)-1-piperdinyl]-1-hydroxybutyl]-α,α-dimethylbenzeneacetic acid hydrochloride, in immediate release form using a formulation similar to that disclosed by N. Webb and G. Hammer in U.S. Pat. No. 4,996,061. However, this formulation failed as a result of unexpected and unacceptable cracking and unacceptable physical strength of the tablets on final compression.

In addition, an attempt was made to prepare a single compression tablet wherein pseudoephedrine hydrochloride sustained release beads and an immediate release form of 4-[4-[4-(hydroxydiphenylmethyl)-1-piperdinyl]-1-hydroxybutyl]-α,α-dimethylbenzeneacetic acid hydrochloride were combined in a single layer tablet. However, this formulation also failed as some of the samples collected during tablet compression and tested for content uniformity did not meet United States Pharmacopeia (USP) requirements.

An object of the present invention is to provide a pharmaceutical composition in oral dosage form as a bilayer tablet which provides immediate release of a piperidinoalkanol compound and sustained release of a sympathomimetic drug that exhibits acceptable bioavailability of each compound. An additional object of the invention is to provide a pharmaceutical composition in bilayer tablet form of high integrity consisting of an immediate release form of a piperidinoalkanol compound and a sustained release form of a sympathomimetic drug, such that the tablet resists cracking on standing, has acceptable physical strength and provides acceptable content uniformity which meets USP requirements. A further object of the present invention is to provide a bilayer tablet which exhibits a dissolution profile of the piperidinoalkanol which is similar to that of ALLEGRA® 60 mg capsules and a dissolution profile of the sympathomimetic drug which is slower than that of SUDAFED® 120 mg tablets.

A novel pharmaceutical composition in the form of a bilayer tablet has now been found which provides efficient and immediate absorption, and bioavailability of a piperidinoalkanol, such as 4-[4-[4-(hydroxydiphenylmethyl)-1-piperdinyl]-1-hydroxybutyl]-α,α-dimethylbenzeneacetic acid hydrochloride, and efficient sustained release and bioavailability of a sympathomimetic drug, such as pseudoephedrine hydrochloride after oral administration thereof. In addition, the novel bilayer tablet of the present invention exhibits acceptable content uniformity under USP requirements, resists cracking on standing and has acceptable physical strength. Furthermore, the novel bilayer tablet of the present invention provides a dissolution profile of 4-[4-[4-(hydroxydiphenylmethyl)-1-piperdinyl]-1-hydroxybutyl]-α,α-dimethylbenzeneacetic acid hydrochloride which is similar to that for ALLEGRA® 60 mg capsules and a dissolution profile for pseudoephedrine hydrochloride which is slower than that for SUDAFED 12 HOUR® 120 mg tablets.

SUMMARY OF THE INVENTION

The present invention provides a pharmaceutical composition in the form of a bilayer tablet comprising,
(a) a first discrete zone made with Formulation (A) which comprises, a therapeutically effective decongestant amount of a sympathomimetic drug, or a pharmaceutically acceptable salt thereof, in an amount of about 18% to about 39% by weight of Formulation (A), and a first carrier base material, the first carrier base material comprising a mixture of;
 (I) carnauba wax in an amount of about 59% to about 81% by weight of Formulation (A); and
 (ii) a suitable antiadherent in an amount of about 0.25% to about 2.00% by weight of Formulation (A);
wherein said first carrier base material provides a sustained release of the sympathomimetic drug; and (b) a second discrete zone made with Formulation (B) which comprises a therapeutically effective antihistaminic amount of a piperidinoalkanol, or a pharmaceutically acceptable salt thereof, in an amount of about 15% to about 30% by weight of Formulation (B) and a second carrier base material, the second carrier base comprising a mixture of;
  (I) a cellulose diluent in an amount of about 27% to about 73% by weight of Formulation (B);
  (ii) pregelatinized starch in an amount of about 15% to about 30% by weight of Formulation (B);
  (iii) a suitable disintegrant in an amount of about 0.25% to about 6.00% by weight of Formulation (B); and
  (iv) a suitable lubricant in an amount of about 0.25% to about 2.00% by weight of Formulation (B);
wherein said second carrier base material provides an immediate release of the piperidinoalkanol or the pharmaceutically acceptable salt thereof.

The present invention further provides a pharmaceutical composition in the form of a bilayer tablet comprising,
  (a) a first discrete zone made with Formulation (A) which comprises, a therapeutically effective decongestant amount of a sympathomimetic drug, or a pharmaceutically acceptable salt thereof in an amount of about 18% to about 39% by weight of Formulation (A), and a first carrier base material, the first carrier base material comprising a mixture of;
    (I) carnauba wax in an amount of about 59% to about 81% by weight of Formulation (A); and
    (ii) a suitable antiadherent in an amount of about 0.25% to about 2.00% by weight of Formulation (A);
  wherein said first carrier base material provides a sustained release of the sympathomimetic drug; and
  (b) a second discrete zone made with Formulation (B) which comprises a therapeutically effective antihistaminic amount of a piperidinoalkanol of the formula;

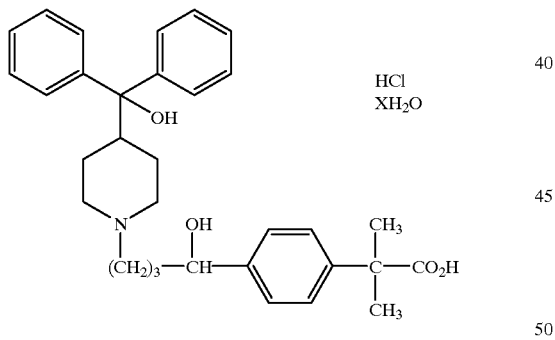

wherein X is a number ranging from about zero to about 5, and the individual optical isomers thereof, in an amount of about 15% to about 30% by weight of Formulation (B) and a second carrier base material, the second carrier base comprising a mixture of;
  (I) a cellulose diluent in an amount of about 27% to about 73% by weight of Formulation (B);
  (ii) pregelatinized starch in an amount of about 15% to about 30% by weight of Formulation (B);
  (iii) a suitable disintegrant in an amount of about 0.25% to about 6.00% by weight of Formulation (B); and
  (iv) a suitable lubricant in an amount of about 0.25% to about 2.00% by weight of Formulation (B);
wherein said second carrier base material provides an immediate release of the piperidinoalkanol or the pharmaceutically acceptable salt thereof.

In addition, the present invention provides a pharmaceutical composition in the form of a bilayer tablet comprising,
  (a) a first discrete zone made with Formulation (A) which comprises, a therapeutically effective decongestant amount of a sympathomimetic drug, or a pharmaceutically acceptable salt thereof in an amount of about 25% to about 33% by weight of Formulation (A), and a first carrier base material, the first carrier base material comprising a mixture of;
    (I) carnauba wax in an amount of about 66% to about 74% by weight of Formulation (A); and
    (ii) a suitable antiadherent in an amount of about 0.50% to about 1.50% by weight of Formulation (A);
  wherein said first carrier base material provides a sustained release of the sympathomimetic drug; and
  (b) a second discrete zone made with Formulation (B) which comprises a therapeutically effective antihistaminic amount of a piperidinoalkanol of the formula;

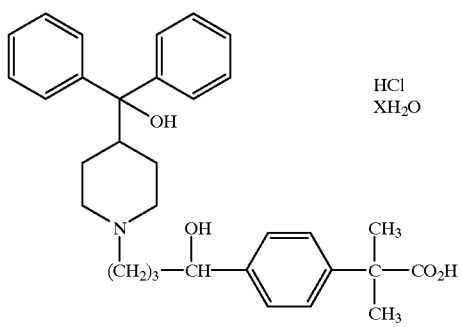

wherein X is a number ranging from about zero to about 5, and the individual optical isomers thereof, in an amount of about 15% to about 24% by weight of Formulation (B) and a second carrier base material, the second carrier base comprising a mixture of;
  (I) a cellulose diluent in an amount of about 43% to about 67% by weight of Formulation (B);
  (ii) pregelatinized starch in an amount of about 15% to about 24% by weight of Formulation (B);
  (iii) a suitable disintegrant in an amount of about 3.20% to about 4.80% by weight of Formulation (B); and
  (iv) a suitable lubricant in an amount of about 0.50% to about 1.00% by weight of Formulation (B);
wherein said second carrier base material provides an immediate release of the piperidinoalkanol or the pharmaceutically acceptable salt thereof.

DETAILED DESCRIPTION OF THE INVENTION

As used herein the terms "piperidinoalkanol compounds" and "piperidinoalkanol compounds and their pharmaceutically acceptable salts" refers to those compounds described by formulas (I), (II) and (III) which are disclosed in U.S. Pat. Nos. 3,878,217, 4,254,129 and 4,285,957 the disclosure of each patent being incorporated herein by reference.

Piperidinoalkanol compounds of formula (I) are those which correspond to the formula;

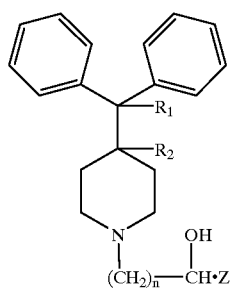

Formula (I)

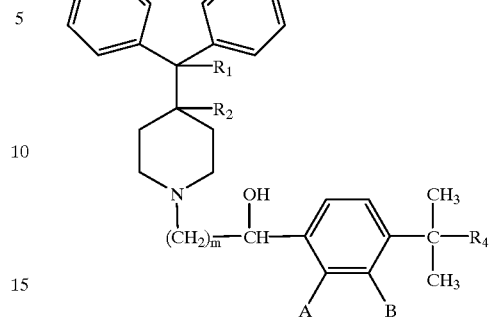

Formula (III)

wherein $R_1$ is hydrogen or hydroxy; $R_2$ is hydrogen; or $R_1$ and $R_2$ taken together form a second bond between the carbon atoms bearing $R_1$ and $R_2$; n is a positive whole integer of from 1 to 3; Z is thienyl, phenyl or substituted phenyl wherein the substituents on the substituted phenyl may be attached at the ortho, meta or para positions of the unsubstituted phenyl ring and are selected from the group consisting of a halogen atom, a straight or branched lower alkyl chain of from 1 to 4 carbon atoms, a lower alkoxy group of from 1 to 4 carbon atoms, a di(lower)alkylamino group, or a saturated monocyclic heterocyclic ring selected from the group consisting of pyrolidino, piperidino, morpholino, or N-(lower)alkylpiperizino, or pharmaceutically acceptable acid addition salts thereof.

Piperidinoalkanol compounds of formula (II) are those which correspond to the formula;

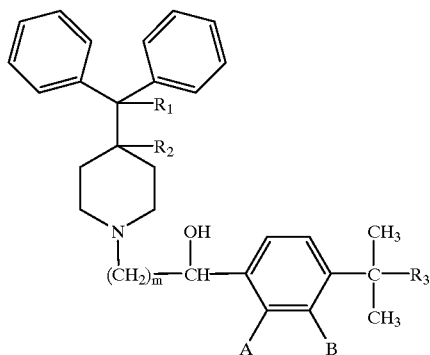

Formula (II)

wherein $R_1$ represents hydrogen or hydroxy; $R_2$ represents hydrogen; or $R_1$ and $R_2$ taken together form a second bond between the carbon atoms bearing $R_1$ and $R_2$; m is an integer of from 1 to 5; $R_3$ is —$CH_3$, or —$CH_2OH$; each A and B is hydrogen or hydroxy; with the provisos that at least one of A or B is hydrogen and one of A or B is other than hydrogen when $R_3$ is —$CH_3$; and pharmaceutically acceptable salts and individual optical isomers thereof.

Piperidinoalkanol compounds of formula (III) are those which correspond to the formula;

wherein $R_1$ represents hydrogen or hydroxy; $R_2$ represents hydrogen; or $R_1$ and $R_2$ taken together form a second bond between the carbon atoms bearing $R_1$ and $R_2$; m is an integer of from 1 to 5; $R_4$ is —$CO_2H$ or —$CO_2$alkyl wherein the alkyl moiety has from 1 to 6 carbon atoms and is straight or branched; each of A and B is hydrogen or hydroxy; with the proviso that at least one of A or B is hydrogen; and pharmaceutically acceptable salts and individual optical isomers thereof.

More specifically, 4-[4-[4-(hydroxydiphenylmethyl)-1-piperdinyl]-1-hydroxybutyl]-α,α-dimethylbenzeneacetic acid hydrochloride of formula (IIIa);

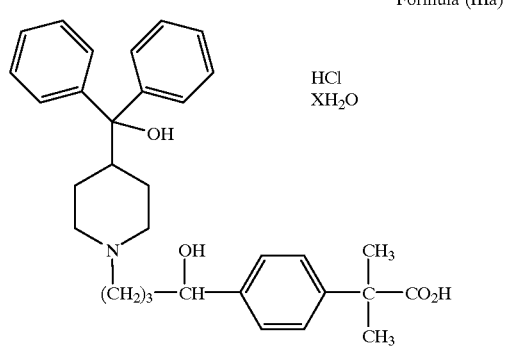

Formula (IIIa)

wherein X is a number ranging from about zero to about 5, and the individual optical isomers thereof, is a preferred piperidinoalkanol compound. The compound 4-[4-[4-(hydroxydiphenylmethyl)-1-piperdinyl]-1-hydroxybutyl]-α,α-dimethylbenzeneacetic acid hydrochloride wherein X is zero or one in formula (IIIa) is the most preferred piperidinoalkanol compound.

In addition, the free base of 4-[4-[4-(hydroxydiphenylmethyl)-1-piperdinyl]-1-hydroxybutyl]-α,α-dimethylbenzeneacetic acid of formula (IIIb)

Formula (IIIb)

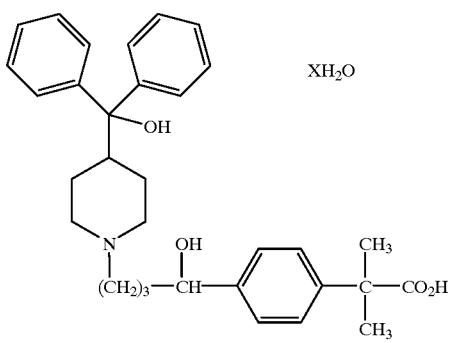

XH₂O wherein X is a number ranging from about zero to about 5, and the individual optical isomers thereof, is also a preferred piperidinoalkanol compound.

Included within the scope of the present invention are the pseudomorphs and polymorphs of the hydrated and anhydrous free base of 4-[4-[4-(hydroxydiphenylmethyl)-1-piperidinyl]-1-hydroxybutyl]-α,α-dimethylbenzeneacetic acid which can be prepared as disclosed in the International Publication No. WO 95/31437 published Nov. 23, 1995. The free base of 4-[4-[4-(hydroxydiphenylmethyl)-1-piperidinyl]-1-hydroxybutyl]-α,α-dimethylbenzeneacetic acid is readily prepared utilizing techniques and procedures well known to one of ordinary skill in the art. For example, the hydrochloride salt of 4-[4-[4-(hydroxydiphenylmethyl)-1-piperidinyl]-1-hydroxybutyl]-α,α-dimethylbenzeneacetic acid is dissolved in methanol and treated with one equivalent of aqueous sodium bicarbonate. After stirring for approximately 5 to 30 minutes, the white solid is collected by filtration, rinsed with water and air dried to provide the dihydrate of the free base of 4-[4-[4-(hydroxydiphenylmethyl)-1-piperidinyl]-1-hydroxybutyl]-α,α-dimethylbenzeneacetic acid.

Illustrative examples of straight or branched alkyl groups having from 1 to 4 carbon atoms referred to herein are methyl, ethyl, n-propyl, isopropyl, n-butyl, isobutyl and t-butyl. Illustrative examples of straight or branched alkyl groups having from 1 to 6 carbon atoms referred to herein are methyl, ethyl, n-propyl, isopropyl, n-butyl, isobutyl, t-butyl, n-pentyl, cyclopentyl, n-hexyl and cyclohexyl. Illustrative examples of lower alkoxy groups of from 1 to 4 carbon atoms referred to herein are methoxy, ethoxy, propoxy, n-butoxy, isobutoxy, sec-butoxy and t-butoxy. The terms "halo", "halogen" or "halide" refers to a fluorine, chlorine, bromine or iodine atom.

The term "pharmaceutically acceptable salt" refers to those salts of formulas (I), (II), (III) and (IIIa) that are not substantially toxic at the dosage administered to achieve the desired effect and do not independently possess significant pharmacological activity. The salts included within the scope of this term are pharmaceutically acceptable acid addition salts of a suitable inorganic or organic acid. Suitable inorganic acids are, for example hydrochloric, hydrobromic, sulfuric and phosphoric acids. Suitable organic acids include carboxylic acids, such as acetic, propionic, glycolic, lactic, pyruvic, malonic, succinic, fumaric, malic, tartaric, citric, cyclamic, ascorbic, maleic, hydroxymaleic, dihydroxymaleic, benzoic, phenylacetic, 4-aminobenzoic, 4-hydroxybenzoic, anthranillic, cinnamic, salicylic, 4-aminosalicyclic, 2-phenoxybenzoic, 2-acetoxybenzoic and mandelic acid, sulfonic acids, such as methanesulfonic, ethanesulfonic and β-hydroxyethanesulfonic acid. In addition, pharmaceutically acceptable salts include those salts of formulas (I), (II), (III) and (IIIa) formed with inorganic and organic bases, such as those of alkali metals, for example sodium, potassium and lithium, alkaline earth metals, for example calcium and magnesium, light metals of group IIIA, for example aluminum, organic amines, for example primary, secondary or tertiary amines, such as cyclohexylamine, ethylamine, pyridine, methylaminoethanol and piperazine. The salts are prepared by conventional means known by one of ordinary skill in the art as, for example, by treating a compound of formulas (I), (II), (III) or (IIIa) with an appropriate acid or base. Such salts can exist in either a hydrated or substantially anhydrous form. The preferred acid addition salts are those prepared from hydrochloric acid, sulfuric acid and tartaric acid.

The term "stereoisomers" is a general term for all isomers of individual molecules that differ only in the orientation of their atoms in space. It includes geometric (cis/trans) isomers, and isomers of compounds with more than one chiral center that are not mirror images of one another (diastereomers). The term "chiral center" refers to a carbon atom to which four different groups are attached. The term "enantiomer", "enantiomeric" or "optical isomer" refers to a molecule that is nonsuperimposable on its mirror image and hence optically active wherein the optical isomer or enantiomer rotates the plane of polarized light in one direction and its mirror image rotates the plane of polarized light in the opposite direction. The term "racemic mixture" or "racemic modification" refers to a mixture of equal parts of enantiomers and which is optically inactive. As used herein the prefixes "(+)" and "(−)" are employed to designate the sign of rotation of the plane of polarized light by the compound, with (+) meaning the compound is dextrorotatory and (−) meaning the compound is levorotatory.

The term "enantiomeric enrichment" refers to the increase in the amount of one enantiomer as compared to its corresponding opposite enantiomer. A convenient method of expressing enantiomeric enrichment achieved is the concept of "enantiomeric excess" or "ee", which is expressed by the following equation;

$$ee = \frac{E^1 - E^2}{E^1 + E^2} \times 100$$

in which $E^1$ is the amount of the first enantiomer and $E^2$ is the amount of the second corresponding enantiomer. For example, where the initial ratio of two enantiomers in a reaction is 50:50 (a racemic mixture) and the reaction produces enantiomeric enrichment with a final ratio of 90:10, then the ee with respect to the first enantiomer is 80%.

Various sympathomimetic drugs, such as pseudoephedrine, phenylephrine and phenylpropanolamine, are recognized by those skilled in the art as therapeutic agents effective in the relief of nasal congestion and are commonly administered concomitantly with antihistamines for relief of nasal congestion associated with allergic rhinitis. These sympathomimetic drugs are generally effective when administered orally in unit dosage form on a four times a day dosage schedule wherein the unit dosage form provides immediate release of the active medicament. For example, the recommended dosage for pseudoephedrine hydrochloride in adults is 60 mg every 6 hours (q.i.d.). In addition, unit dosage forms containing sympathomimetic drugs can be formulated to provide prolonged release of the active medicament so as to allow the effective daily dose to be administered on a less frequent dosage schedule. For example, the recommended dosage for pseudoephedrine hydrochloride in a sustained release formulation can be 120 mg twice daily (b.i.d.).

As used herein the term "sympathomimetic drug" refers to those sympathomimetic agents which are therapeutically effective in providing relief of nasal congestion in a patient suffering therefrom. These agents include, but are not limited to, pseudoephedrine, phenylephrine, and phenylpropanolamine. As is well recognized and appreciated by those skilled in the art, these sympathomimetic drugs can be used according to the present invention as free amines or as pharmaceutically acceptable salts thereof.

A therapeutically effective decongestant amount of a sympathomimetic drug is that amount which produces the desired decongestant therapeutic response upon oral administration and can be readily determined by one skilled in the art by use of conventional techniques and by observing results obtained under analogous circumstances. In determining the therapeutically effective decongestant amount or dose, a number of factors are considered by the attending diagnostician, including, but not limited to: the species of mammal; its size, age, and general health; the response of the individual patient; the particular compound administered; the mode of administration; the bioavailability characteristics of the preparation administered; the dose regimen selected; the use of concomitant medication; and other relevant circumstances.

A therapeutically effective decongestant amount of a sympathomimetic drug will vary from about 1 mg to about 200 mg. Preferred amounts will vary from about 5 mg to about 150 mg, with about 120 mg administered twice daily being most preferred.

It is understood that a therapeutically effective decongestant amount of a sympathomimetic drug is present in Formulation (A). The carrier base material of Formulation (A) provides a prolonged or sustained release of the active medicament whereas the carrier base material of Formulation (B) provides an immediate release of the active medicament. As used herein the term "sustained release" refers to a property of the pharmaceutical composition wherein the absorption and bioavailability of the active medicament is maintained in a time-release pattern such that therapeutically effective decongestant amounts of the sympathomimetic drug are bioavailable over an extended period of time. As used herein the term "immediate release" refers to a property of the pharmaceutical composition wherein the entire dose of active medicament is made bioavailable without substantial delay. A unit dose is that amount of the pharmaceutical composition which is individually administered to a patient. In addition, it is appreciated by one of ordinary skill in the art that the pharmaceutical compositions of the present invention are useful as antihistamines, antiallergy agents, bronchodilators and in the treatment of urticaria.

As used herein, the term "patient" refers to a warm-blooded animal, such as a mammal, which is in need of an antihistamine, antiallergy agent, bronchodilator or requires treatment of urticaria. It is understood that humans, mice, rats and dogs are included within the term "patient".

As used herein, the term "cellulose diluent" includes microcrystalline cellulose, Avicel PH101, Avicel PH102, Avicel PH301, Avicel PH302, Avicel PH200, Avicel PH112, Avicel PH113, Avicel PH103, Avicel PH105 and the like. The preferred cellulose diluent is microcrystalline cellulose, Avicel PH101 and Avicel PH102, and the most preferred cellulose diluent is a combination of Avicel PH101 and Avicel PH102. It is especially preferred that the Avicel PH101 and Avicel PH102 mixture comprise about 12% Avicel PH101 and about 88% Avicel PH102.

As used herein, the term "suitable antiadherent" includes stearic acid, cetyl alcohol, stearyl alcohol, paraffin, white wax, glycerin, lanolin, talc, mineral oil and the like. The preferred suitable antiadherent is stearic acid.

As used herein, the term "suitable disintegrant" includes croscarmellose sodium, crospovidone, alginic acid, sodium alginate, methacrylic acid DVB, cross-linked PVP, microcrystalline cellulose, polacrilin potassium, sodium starch glycolate, starch, pregelatinized starch and the like. The preferred suitable disintegrant is croscarmellose sodium.

As used herein, the term "suitable lubricant" includes magnesium stearate, calcium stearate, zinc stearate, stearic acid, talc, hydrogenated vegetable oil and the like. The preferred suitable lubricant is magnesium stearate.

As used herein, the term "suitable glidant" includes silicon dioxide, talc and the like. The preferred suitable glidant is silicon dioxide.

The term "micronization" refers to the process of increasing the particle surface area of the piperidinoalkanol compounds or their pharmaceutically acceptable salts to greater than about 1.0 $m^2/g$. Micronization of the piperidinoalkanol compounds of formulas (I) through (IIIb) is readily performed by one of ordinary skill in the art, for example, as disclosed by T. Ortyl, et al. in WO 96/26726 published Sep. 6, 1996.

The piperidinoalkanol compounds of formulas (I) through (IIIb) when micronized have a particle surface area of greater than about 1.0 $m^2/g$. The preferred particle surface area when micronized is about 2 to 10 $m^2/g$, the most preferred particle surface area when micronized is about 2.0 to 5 $m^2/g$ and the most especially preferred particle surface area of the piperidinoalkanol compounds of formulas (I) through (IIIb) when micronized is about 2.2 $m^2/g$. The piperidinoalkanol compounds of formulas (I) through (IIIb) which are not subjected to micronization have a particle surface area of less than about 1.0 $m^2/g$.

A therapeutically effective antihistaminic amount of a piperidinoalkanol compound of formulas (I) through (IIIb) is that amount which produces the desired therapeutic response (ie., antihistaminic, antiallergic, bronchodilatory effect, or reduction or elimination of urticaria) upon oral administration according to a single or multiple dosage regimen. A therapeutically effective antihistaminic amount of a piperidinoalkanol compound of formulas (I) through (IIIb) may vary over a wide range IS from about 0.1 mg to about 240 mg. The preferred therapeutically effective antihistaminic amount of a piperidinoalkanol compound of formulas (I) through (IIIb) will vary from about 20 mg to about 70 mg with about 60 mg administered twice daily being most preferred. The therapeutically effective antihistaminic amount can be readily determined by the attending diagnostician, as one skilled in the art, by the use of known techniques and by observing results obtained under analogous circumstances as described above for the sympathomimetic drugs.

It is understood that a therapeutically effective antihistaminic amount of a piperidinoalkanol compound of formulas (I) through (IIIb) is present in Formulation (B) of the pharmaceutical composition of the present invention. This Formulation (B) provides for immediate release of the active medicament.

In a preferred embodiment of the present invention with respect to the piperidinoalkanol in Formulation (B), about 60 mg of 4-[4-[4-(hydroxydiphenylmethyl)-1-piperdinyl]-1-hydroxybutyl]-α,α-dimethylbenzeneacetic acid hydrochloride is preferred. In a preferred embodiment of the present invention with respect to the sympathomimetic drug in Formulation (A), about 120 mg of pseudoephedrine hydrochloride is preferred.

As used herein a layered tablet is a tablet which is made up of two or more distinct layers or discrete zones of granulation compressed together with the individual layers lying one on top of another. Layered tablets have the appearance of a sandwich because the edges of each layer or zone is exposed. Such conventional layered tablets are generally prepared by compressing a granulation onto a previously compressed granulation. The operation may be repeated to produce multilayered tablets of more than two layers. In a preferred embodiment of the present invention, the tablet consists of two layers wherein one layer is made from Formulation (A) and the other layer is made from Formulation (B), resulting in a bilayer tablet.

Formulation (A) and Formulation (B) of the pharmaceutical compositions of the present invention optionally may contain one or more other pharmaceutically acceptable excipients. These excipients are therapeutically inert ingredients such as are well known and appreciated in the art. As used herein the term "inert ingredient" refers to those therapeutically inert ingredients that are well known in the art of pharmaceutical science which can be used singly or in various combinations, and include, for example, binders, diluents, lubricants, glidants, sweetening agents, disintegrants, coloring agents, flavoring agents, antioxidants, solubilizing agents, coating agents and the like, as are disclosed in The United States Pharmacopeia, XXII, 1990, (1989 The United States Pharmacopeial Convention, Inc.), pages 1857–1859, which is incorporated herein by reference. For example, the following inert ingredients can be utilized singly or in various combinations; binders such as gelatin, polyvinylpyrrolidone (PVP), pregelatinized starch, povidone; diluents such as calcium carbonate, lactose, starch, microcrystalline cellulose, and the like; lubricants such as magnesium stearate, calcium stearate, zinc stearate, stearic acid, talc, hydrogenated vegetable oil and the like; glidants such as silicon dioxide, talc and the like; disintegrants such as alginic acid, methacrylic acid DVB, cross-linked PVP, microcrystalline cellulose, croscarmellose sodium, crospovidone, polacrilin potassium, sodium starch glycolate, starch, pregelatinized starch and the like; sweetening agents; coloring agents; flavoring agents; antioxidants; and the like.

Preferred compositions of the present invention are those wherein a cellulose diluent, pregelatinized starch, croscarmellose sodium and magnesium stearate are present with 4-[4-[4-(hydroxydiphenylmethyl)-1-piperdinyl]-1-hydroxybutyl]-α,α-dimethylbenzeneacetic acid hydrochloride in the immediate release layer of Formulation (B), and wherein carnauba wax, stearic acid and colloidal silicon dioxide are present with pseudoephedrine hydrochloride in the sustained release layer of Formulation (A).

Preferred amounts of 4-[4-[4-(hydroxydiphenylmethyl)-1-piperdinyl]-1-hydroxybutyl]-α,α-dimethylbenzeneacetic acid hydrochloride, cellulose diluent, pregelatinized starch, croscarmellose sodium and magnesium stearate in Formulation (B) are combined in amounts of from about 15% to about 30%, about 27% to about 73%, about 15% to about 30%, about 0.25% to about 6.00% and about 0.25% to about 2.00%, respectively, by weight of the composition, with about 16% to about 24%, about 43% to about 67, about 15% to about 24%, about 3.20% to about 4.80% and about 0.50% to about 1.00%, respectively, by weight of the composition, being most preferred, and about 17.09%, about 61.67%, about 17.09%, about 3.42% and about 0.75%, respectively, being most especially preferred.

Preferred amounts of pseudoephedrine hydrochloride, carnauba wax, stearic acid flakes and colloidal silicon dioxide in Formulation (A) are combined in amounts of from about 18% to about 39%, about 59% to about 81%, about 0.25% to about 2.00%, and 0.00% to about 3.00%, respectively, by weight of the composition, with about 25% to about 33%, about 66% to about 74%, about 0.50% to about 1.50% and 0.00% to about 0.75%, respectively, by weight of the composition, being most preferred, and about 28.17%, about 70.42%, about 1.15% and about 0.25%, respectively, being most especially preferred.

The piperidinoalkanol compounds of formulas (I) through (IIIb) are readily prepared by one of ordinary skill in the art, for example, utilizing the techniques and procedures described in U.S. Pat. Nos. 3,878,217, 4,254,129 and 4,285,957, which are hereby incorporated by reference, and International Application Number PCT/US93/02103 published Oct. 28, 1993, WO 93/21156, International Application Number PCT/US94/05982, published Jan. 5,1995, WO 95/00480 and International Application Number WO 95/31437, published Nov. 23, 1995.

The components of the pharmaceutical composition according to the present invention are brought together into a bilayer tablet for oral administration according to standard practice and procedures well known to one of ordinary skill in the art using conventional formulation and manufacturing techniques such as that described in the following examples. The following examples are understood to be illustrative only and are not intended to limit the scope of the present invention in any way. The reagents and starting materials are available to one of ordinary skill in the art. As used herein, the following terms have the indicated meanings: "rsd" refers to percent relative standard deviation; "kg" refers to kilograms; "g" refers to grams; "mg" refers to milligrams; "$\mu$" refers to micrograms; "$m^2/g$" refers to square meters per gram and is used as a measurement of particle surface area; "mmol" refers to millimoles; "L" refers to liters; "mL" refers to milliliters; "$\mu L$" refers to microliters; "cm" refers to centimeters; "M" refers to molar; "mM" refers to millimolar; "$\mu M$" refers to micromolar; "nM" refers to nanomolar; "eq" refers to equivalents; "N" refers to normal; "ppm" refers to parts per million; "° C." refers to degrees Celsius; "° F" refers to degrees Fahrenheit; "mm Hg" refers to millimeters of mercury; "kPa" refers to kilopascals; "psi" refers to pounds per square inch; "bp" refers to boiling point; "mp" refers to melting point; "dec" refers to decomposition; "HPLC" refers to high performance liquid chromatography; "RPM" refers to revolutions per minute; "hr" or refers to hours; "min' refers to minutes; "Kp" refers to Kilopond and "sec" refers to seconds.

TABLE 1

Composition of the Bilayer Tablet

| Component | Weight (mg/tablet) |
| --- | --- |
| Immediate Release Layer | |
| Piperidinoalkanol[1] | 60.00 |
| Microcrystalline Cellulose (Avicel PH 101) | 26.00 |
| Pregelatinized Starch | 60.00 |
| Microcrystalline Cellulose (Avicel PH 102) | 190.5 |
| Croscarmellose Sodium | 12.00 |
| Magnesium Stearate | 2.633 |
| Water, purified[2] | (60.00) |
| Total Layer Weight | 351.1 |

TABLE 1-continued

Composition of the Bilayer Tablet

| Component | Weight (mg/tablet) |
| --- | --- |
| Sustained Release Layer | |
| Sympathomimetic Drug[3] | 120.0 |
| Carnauba Wax | 300.0 |
| Stearic Acid Flakes | 4.899 |
| Colloidal Silicon Dioxide | 1.065 |
| Total Layer Weight | 426.0 |
| Total Core Tablet Weight | 777.1 |
| Aqueous Coating Suspension | |
| OPADRY ® YS-1-7006 | 23.31 |
| Water, purified[2] | (170.9) |
| Total Coated Tablet Weight | 800.4 |

[1]4-[4-[4-(Hydroxydiphenylmethyl)-1-piperdinyl]-1-hydroxybutyl]-α
[2]Removed during processing. Amount of water may be varied during processing if necessary to achieve the desired granulation characteristics.
[3]Pseudoephedrine hydrochloride.

Pilot Scale Process Used to Manufacture Bilayer Tablets

The manufacture of the bilayer tablets at pilot scale is summarized as follows. The pseudoephedrine HCl granulation is manufactured by adding pseudoephedrine HCl to a melted mixture of carnauba wax and stearic acid with mixing. The liquid wax mixture is then poured onto trays in sheets and allowed to congeal as the wax cools. The congealed wax is then milled and blended with the colloidal silicon dioxide in an in-bin blender. The 4-[4-[4-(hydroxydiphenylmethyl)-1-piperdinyl]-1-hydroxybutyl]-α, α-dimethylbenzeneacetic acid hydrochloride granulation is manufactured using a high intensity granulator. The granulation is dried in a fluid bed drier and milled. The final blend components are added and blended in an in-bin blender. The bilayer tablets are compressed on a bilayer tablet press with the pseudoephedrine HCl granulation compressed as the first layer and 4-[4-[4-(hydroxydiphenylmethyl)-1-piperdinyl]-1-hydroxybutyl]-α,α-dimethylbenzeneacetic acid hydrochloride final blend compressed as the second or top layer. The compressed tablets are then film coated with a clear coating in an Accela-Cota. Total process time required to manufacture film coated tablets is approximately 33 hours for a pilot scale batch of 130,000 tablets.

Pseudoephedrine HCL Granulation.

The quantities of components used to manufacture pseudoephedrine HCl granulation (80 kg batch size) are listed in Table 2. The carnauba wax is melted while continuously mixing at approximately 85–90° C. in a 100 gallon Hamilton hot water jacketed stainless steel tank. The jacket water temperature is set at approximately 100° C. After all the carnauba wax is melted, stearic acid flakes are added and allowed to melt. Pseudoephedrine HCl is screened through a 30 mesh screen utilizing a Stokes Oscillating Granulator. The screened pseudoephedrine HCl is slowly added to the wax melt while continuously mixing with a Lightnin propeller type mixer. The temperature of the melt is held at approximately 90° C. during pseudoephedrine HCl addition. Once all the screened pseudoephedrine HCl is added to the melted wax, the temperature is raised to 92° C. and continuously mixed for 10 minutes. Approximate process time to manufacture pseudoephedrine HCl/liquid wax suspension is 5 hours.

The pseudoephedrine HCl/liquid wax suspension is then dispensed onto stainless steel trays to a thickness of approximately ¼ inch and held at room temperature until solidified and cool to touch, approximately 2 hours. The solidified pseudoephedrine HCl wax matrix is stored in polyethylene lined fiber drums at room temperature for a minimum of 12 hours prior to milling to ensure that the wax matrix is adequately cooled.

The congealed wax is milled with the knives forward, at 2500 rpm, through a Fitzmill equipped with a #0065 drilled holed screen. The milled pseudoephedrine HCl granulation is added to a 200 Liter In-Bin Blending Tote. The required amount of colloidal silicon dioxide is screened through a 20 mesh hand screen and added to the 200 Liter Tote. The components of the tote bin are mixed for 70 revolutions (counts) at 18 rpm using a CMS In-Bin Blender. The final blend is stored in polyethylene lined fiber drums until needed for compression. Approximate process time for milling and blending steps is 1 hour.

4-[4-[4-(Hydroxydiphenylmethyl)-1-piperdinyl]-1-hydroxybutyl]-α,α-dimethylbenzeneacetic acid Hydrochloride Granulation and Final Blend.

Table 3 lists the ingredients and quantities utilized in manufacturing the 4-[4-[4-(hydroxydiphenylmethyl)-1-piperdinyl]-1-hydroxybutyl]-α,α-dimethylbenzeneacetic acid hydrochloride granulation and the final blend. The 4-[4-[4-(hydroxydiphenylmethyl)-1-piperdinyl]-1-hydroxybutyl]-α,α-dimethylbenzeneacetic acid hydrochloride granulation is prepared utilizing a Fielder PMA 300 Liter High Shear Mixer/Granulator. The 4-[4-[4-(hydroxydiphenylmethyl)-1-piperdinyl]-1-hydroxybutyl]-α, α-dimethylbenzeneacetic acid hydrochloride, croscarmellose sodium, pregelatinized starch and microcrystalline cellulose (Avicel PH101) are added to the fielder bowl and dry blended for 5 minutes with the impeller set at 110 RPM and the chopper off. The purified water is then added to the dry mix at a rate of 5.7 kg/min with the impeller speed set at 110 RPM and the chopper at 3600 RPM. The granulation is mixed for 30 seconds after the water addition is completed.

The granulation is divided into approximately equal halves and dried as two sub-batches in a Glatt Fluid Bed Dryer GPCG 30. The inlet air temperature is maintained at 80° C. and the dewpoint is set at 9° C. The process air flow is set at 1050 m³/hr initially and gradually reduced over the drying time to 550 m³/hr. The granulation is dried to a moisture content of 2–3% as determined by a Computrac set at 125° C. The ending product temperature is approximately 65° C. and the drying time is approximately 160 minutes total drying time. The final moisture content of the dried granulation is approximately 2.5%.

Each sub-batch of 4-[4-[4-(hydroxydiphenylmethyl)-1-piperdinyl]-1-hydroxybutyl]-α,α-dimethylbenzeneacetic acid hydrochloride granulation is separately milled through a 1532-0050 drilled holed screened using a Fitzmill set at medium speed with the knives in the forward position. Both sub-batches of granulation are blended together for 3 minutes in a 5 cubic foot Patterson Kelly V-Blender. The milled blends are stored in polyethylene lined fiber drums until needed for final blending. Approximate process time through the milling and blending step for the 4-[4-[4-(hydroxydiphenylmethyl)-1-piperdinyl]-1-hydroxybutyl]-α, α-dimethylbenzeneacetic acid hydrochloride granulation is 8 hours.

The formulation for the 4-[4-[4-(hydroxydiphenylmethyl)-1-piperdinyl]-1-hydroxybutyl]-α, α-dimethylbenzeneacetic acid hydrochloride final blend is listed in Table 3. The 4-[4-[4-(hydroxydiphenylmethyl)-1-piperdinyl]-1-hydroxybutyl]-α,α-dimethylbenzeneacetic acid hydrochloride final blend is manufactured using a 200

Liter In-Bin Blending Tote. The microcrystalline cellulose (Avicel PH102), croscarmellose sodium (Ac-Di-Sol) and the milled 4-[4-[4-(hydroxydiphenylmethyl)-1-piperdinyl]-1-hydroxybutyl]-α,α-dimethylbenzeneacetic acid hydrochloride granulation from above are charged into the tote bin. The components are blended for 140 revolutions (counts) at 18 rpm. Magnesium stearate is screened through a 30 mesh hand screen and added to the 200 liter tote bin and is blended for 70 counts at 18 rpm. The final blend is stored in polyethylene lined fiber drums until needed for compression. Approximate process time for final blend process is 0.5 hours.

Bilayer Tablet Compression.

The bilayer tablet batch is manufactured utilizing a 35 Station Manesty BB4 Bi-Layer Rotary Tablet Press. Tablets are compressed using 0.3125 inch×0.7500 inch capsule shaped standard concave tooling. The tablet batch size is 180,000 tablets manufactured from 76.7 kg of pseudoephedrine HCl granulation and 63.2 kg of 4-[4-[4-(hydroxydiphenylmethyl)-1-piperdinyl]-1-hydroxybutyl]-α,α-dimethylbenzeneacetic acid hydrochloride final blend. The average press speed is approximately 640 tablets per minute. The total compression time is approximately 5 hours.

The pseudoephedrine HCl granulation is compressed into the first layer at a target weight of 426 mg per tablet. The average target tablet hardness (Key Hardness Tester, tablet tested across width) for the pseudoephedrine HCl layer is about 8 kp. The second layer which consists of the 4-[4-[4-(hydroxydiphenylmethyl)-1-piperdinyl]-1-hydroxybutyl]-α,α-dimethylbenzeneacetic acid hydrochloride final blend is added to the first layer for a total tablet target weight of 777.1 mg (which is equivalent to 351.1 mg/tablet of the 4-[4-[4-(hydroxydiphenylmethyl)-1-piperdinyl]-1-hydroxybutyl]-α,α-dimethylbenzeneacetic acid hydrochloride final blend). The bilayer tablet is compressed to a target hardness of about 20 kp (Key hardness Tester, tablet tested across length).

Coating

The compressed bilayer tablets are coated in a 48 inch Accela-Cota (101.0 kg uncoated tablets, approximately 130,000 tablets) using a two gun spray system at a pan speed of 10.5 rpm. The tablets are coated using a 12% w/w coating solution of clear coat OPADRY® YS-1-7006 which contains hydroxypropyl methylcellulose and polyethylene glycol. The coating suspension is filtered through a 60 mesh screen prior to use. The tablets are coated with 25.25 kg of coating solution. The tablets are coated at an outlet air temperature of approximately 41° C. with a range of 39.6–41.9° C. The inlet air temperature generally ranges from 55–62° C. and a supply air flow rate of 1700–1800 cubic feet per minute is used. The coating solution flow rate is started at approximately 230 g/min and increased periodically to reach a final spray rate of approximately 390 g/min. An atomizing air pressure of 50 psi is used during spraying of the coating solution. The total coating process time is approximately 1.5 hours.

TABLE 2

Pseudoephedrine HCl Granulation Formulation Pilot Scale.

| Component | Quantity (mg/gm) | Quantity (kg/80 kg Batch Size) |
|---|---|---|
| Pseudoephedrine HCl | 281.7 | 22.54 |
| Carnauba Wax, NF | 704.3 | 56.34 |
| Stearic Acid Flakes, NF | 11.50 | 0.920 |
| Colloidal Silicon Dioxide, NF | 2.50 | 0.200 |

TABLE 3

Piperidinoalkanol[1] Final Blend Formulation Pilot Scale.

| Component | Quantity (mg/gm) | Quantity (kg/65 kg Blend Batch Size) |
|---|---|---|
| ***Piperidinoalkanol[1] Granulation | 438.6 | 28.51 |
| Microcrystalline Cellulose (Avicel PH 102) | 542.5 | 35.26 |
| Croscarmellose, Sodium | 11.40 | 0.741 |
| Magnesium Stearate | 7.5 | 0.4875 |

| ***Piperidinoalkanol[1] Granulation | | |
|---|---|---|
| Component | Quantity (mg/gm) | Quantity (kg/60 kg Granulation) |
| Piperidinoalkanol[1] Drug Substance | 389.6 | 23.38 |
| Croscarmellose, Sodium | 51.95 | 3.117 |
| Pregelatinized Starch | 389.6 | 23.38 |
| Microcrystalline Cellulose (Avicel PH 101) | 168.8 | 10.13 |
| Water, Purified USP[2] | 389.6 | 23.38 |

[1]4-[4-[4-(Hydroxydiphenylmethyl)-1-piperdinyl]-1-hydroxybutyl]-α,α-dimethylbenzeneacetic acid hydrochloride.
[2]Water is removed during the process and does not appear in the final product. The amount of water may be varied to achieve suitable granulation.

Commercial Scale Process Used to Manufacture the Bilayer Tablets

Manufacture of the bilayer tablets at commercial scale is summarized as follows. Pseudoephedrine HCl granulation is manufactured by adding pseudoephedrine HCl to melted carnauba wax with mixing. The liquid wax mixture is pumped through a droplet forming stainless steel tube (Rotoform® unit) onto a rotating stainless steel chilled belt. The congealed droplets of wax (pastilles) are discharged off the end of the rotating belt. The pastilles are then milled and blended with the colloidal silicon dioxide in an in-bin blender. The 4-[4-[4-(hydroxydiphenylmethyl)-1-piperdinyl]-1-hydroxybutyl]-α,α-dimethylbenzeneacetic granulation is manufactured using a high intensity granulator. The granulation is dried in a fluid bed drier and milled. The final blend components are added and blended in an in-bin blender. The bilayer tablets are compressed on a two layer tablet press with the pseudoephedrine HCl granulation compressed as the first layer and 4-[4-[4-(hydroxydiphenylmethyl)-1-piperdinyl]-1-hydroxybutyl]-α,α-dimethylbenzeneacetic acid hydrochloride final blend compressed as the second or top layer. The compressed tablets are then film coated with a clear coating in an Accela-Cota. Total process time required to manufacture film coated tablets is approximately 50 hours for a commercial scale batch of 1,374,000 tablets.

Pseudoephedrine HCl Granulation.

The quantities of components used to manufacture pseudoephedrine HCl granulation (600 kg batch size) are listed in Table 4. The carnauba wax is melted while continuously mixing at approximately 85–90° C. in a 300 gallon jacketed stainless steel tank. The jacket water temperature is set at approximately 120° C. After all the carnauba wax is melted, stearic acid flakes are added and allowed to melt. Pseudoephedrine HCl is screened through a 30 mesh screen utilizing a Stokes Oscillating Granulator (Model 43-6). The screened pseudoephedrine HCl is slowly added to the wax melt while continuously mixing with a propeller type mixer (Sew-Eurodrive mixer). The temperature of the melt is held at approximately 92° C. during pseudoephedrine HCl addition. Once all the screened pseudoephedrine HCl is added to the melted wax, the temperature is raised to 95° C. and continuously mixed for a minimum of 20 minutes and mixing is continued until completion of the wax congealing step and the temperature is maintained at 95° C. during the congealing step. Approximate process time to manufacture the pseudoephedrine HCl/liquid wax suspension is 6 hours.

The pseudoephedrine HCl/liquid wax suspension is pumped using a hot water jacketed positive displacement pump (Wauakasha Model 6) through ⅜ inch (internal diameter) hot water (110° C.) jacketed stainless steel lines to a droplet forming stainless steel tube (Sandvik Rotoform® 3000, Model LV). A 20 mesh screen is placed in line of the liquid wax suspension feed to protect the Rotoform®. The Rotoform® has a Shell Bore of 2.0 mm, Shell Pitch of 8.0 mm, a Triangular Offset Shell Geometry and a Bar Slot Width of 6.0 mm. The Rotoform® is heated with 110° C. hot water through the fixed cylindrical stator body which has a 1 inch recess for liquid wax flow through its entire body.

The rotating Rotoform® unit is positioned over the rotating Sandvik stainless steel chilled belt such that droplets of the liquid wax mixture fall onto the moving belt. The Sandvik stainless steel chilled belt is utilized for the wax cooling (congealing) process. The belt is chilled with water sprayed from the bottom side of the belt. The stainless steel chilled belt is 32 inches wide and has a cooling zone 24 feet long. The front pulley on the belt is heated to 65° C. The Rotoform® unit is set approximately 2 mm above the moving belt. A belt speed and Rotoform® speed of 70 feet/minute are used along with a cooling water temperature of 15° C. The pseudoephedrine HCl/liquid wax suspension is pumped at a rate of approximately 5 kg/min onto the belt. The congealed droplets of wax (pastilles) approximately 5 mm in diameter are discharged off the end of the rotating belt at a temperature of approximately 20° C. The congealed wax pastilles are milled with the knives forward, at 3000 rpm, through a Fitzpatrick DAS06 mill equipped with a 0065 drilled holed screen. Approximate process time for the wax congealing and milling step is 3 hours.

The milled pseudoephedrine HCl granulation is charged into an 1800 Liter In-Bin Blending Tote (Gallay). The colloidal silicon dioxide is screened through a 20 mesh hand screen and added to the 1800 Liter Tote. The contents of the bin are blended for 140 revolutions (counts) at 14 rpm using a CMS In-Bin Blender. The final blend is stored in the tote bin until needed for tablet compression. The approximate process time for the pseudoephedrine HCl granulation blend step is 1 hour.

4-[4-[4-(hydroxydiphenylmethyl)-1-piperdinyl]-1-hydroxybutyl]-α,α-dimethylbenzeneacetic acid Hydrochloride Granulation and Final Blend.

Table 5 lists the ingredients and quantities utilized in manufacturing the 4-[4-[4-(hydroxydiphenylmethyl)-1-piperdinyl]-1-hydroxybutyl]-α,α-dimethylbenzeneacetic acid hydrochloride granulation and the final blend. The 4-[4-[4-(hydroxydiphenylmethyl)-1-piperdinyl]-1-hydroxybutyl]-α,α-dimethylbenzeneacetic acid hydrochloride granulation is prepared utilizing a Fielder PMA 800 Liter High Shear Mixer/Granulator. The 4-[4-[4-(hydroxydiphenylmethyl)-1-piperdinyl]-1-hydroxybutyl]-α, α-dimethylbenzeneacetic acid hydrochloride, croscarmellose sodium, pregelatinized starch and microcrystalline cellulose (Avicel PH101) are added to the fielder bowl and dry blended for 5 minutes with the impeller set at 116 RPM and the chopper off. The purified water is then added to the dry mix at a rate of 15 kg/min with the impeller speed set at 116 RPM and the chopper at 1800 RPM. After the water is added, the granulation is mixed for a total of 6 minutes from the start of water addition. The chopper speed is increased to 2800 RPM with the impeller set at 116 RPM and the granulation is mixed an additional 60 seconds and then discharged from the granulator into the fluid bed drier product bowl.

The granulation is dried in a Glatt Fluid Bed Dryer GPCG 300. The inlet air temperature is maintained at 80° C. and the dewpoint is set at 9° C. The process air flow is set at 3800 m$^3$/hr initially and gradually reduced over the drying time to 2900 m$^3$/hr. The granulation is dried to a moisture content of 2-4% as determined by a Computrac set at 115° C. The ending product temperature is approximately 66° C. and the drying time is approximately 100 minutes total drying time. The final moisture content of the dried granulation is approximately 3.0%. The dried 4-[4-[4-(hydroxydiphenylmethyl)-1-piperdinyl]-1-hydroxybutyl]-α,α-dimethylbenzeneacetic acid hydrochloride granulation is milled through a 1532-0050 drilled holed screened using a Fitzmill set at medium speed with the knives in the forward position. The granulation is milled into an 1800 Liter In-Bin Blending Tote (Gallay). The approximate process time for the 4-[4-[4-(hydroxydiphenylmethyl)-1-piperdinyl]-1-hydroxybutyl]-α,α-dimethylbenzeneacetic acid hydrochloride granulation through the milling step is 5 hours.

The formulation for the 4-[4-[4-(hydroxydiphenylmethyl)-1-piperdinyl]-1-hydroxybutyl]-α, α-dimethylbenzeneacetic acid hydrochloride final blend is listed in Table 4. The microcrystalline cellulose (Avicel PH102) and croscarmellose sodium (Ac-Di-Sol) are charged into the tote bin containing the 4-[4-[4-(hydroxydiphenylmethyl)-1-piperdinyl]-1-hydroxybutyl]-α, α-dimethylbenzeneacetic acid hydrochloride milled granulation. The contents are blended for 140 revolutions (counts) at 14 rpm using a CMS In-Bin Blender. Magnesium stearate is screened through a 30 mesh hand screen and added to the 1800 liter tote bin and the contents are blended for 70 counts at 14 rpm using a CMS In-Bin Blender. The final blend is stored in the tote bin until needed for tablet compression. The approximate process time for the 4-[4-[4-(hydroxydiphenylmethyl)-1-piperdinyl]-1-hydroxybutyl]-α, α-dimethylbenzeneacetic acid hydrochloride final blend is 1 hour.

Bilayer Tablet Compression.

The bilayer tablet batch is manufactured utilizing a 51 Station Hata Bi-Layer Rotary Tablet Press, Model HT-HX51 LD-U. Tablets are compressed using 0.3125 inch×0.7500 inch capsule shaped standard concave tooling. The tablet batch size is 1,374,000 tablets manufactured from 585.3 kg of pseudoephedrine HCl granulation and 482.4 kg of 4-[4-[4-(hydroxydiphenylmethyl)-1-piperdinyl]-1-hydroxybutyl]-α,α-dimethylbenzeneacetic acid hydrochloride final blend. The average press speed is approximately 1200 tablets per minute. The total compression time is approximately 19 hours. Both the pseudoephedrine HCl granulation and the 4-[4-[4-(hydroxydiphenylmethyl)-1-piperdinyl]-1-hydroxybutyl]-α,α-dimethylbenzeneacetic acid hydrochloride final blend are fed to the press from the tote bins used for blending by using a Gallay bin drop station.

The pseudoephedrine HCl granulation is compressed into the first layer at a target weight of 426 mg per tablet. The powder feeder for the pseudoephedrine HCl granulation is operated at 75%. The target thickness for the pseudoephedrine HCl layer is 0.162 inches with an average tablet hardness (Key Hardness Tester, tablet tested across width) of about 8 kp. The second layer which consisted of the 4-[4-

[4-(hydroxydiphenylmethyl)-1-piperdinyl]-1-hydroxybutyl]-α,α-dimethylbenzeneacetic acid hydrochloride final blend is added to the first layer for a total tablet target weight of 777.1 mg (which is equivalent to 351.1 mg/tablet of the 4-[4-[4-(hydroxydiphenylmethyl)-1-piperdinyl]-1-hydroxybutyl]-α,α-dimethylbenzeneacetic acid hydrochloride final blend). The powder feeder for the 4-[4-[4-(hydroxydiphenylmethyl)- 1-piperdinyl]-1-hydroxybutyl]-α,α-dimethylbenzeneacetic acid hydrochloride blend is operated at 100%. The bilayer tablet is compressed to a target thickness of 0.240 inches with an average hardness of about 20 kp (Key hardness Tester, tablet tested across length).

Coating

The compressed bilayer tablets are coated in a 48 inch Accela-Cota as 10 sub-batches of approximately 106.8 kg uncoated tablets (approximately 137,400 tablets) using a three gun spray system at a pan speed of 11 RPM. The tablets are coated using a 12% w/w coating solution of clear coat OPADRY® YS-1-7006 which contains hydroxypropyl methylcellulose and polyethylene glycol. The tablets are coated with 26.70 kg of coating solution. The tablets are coated at an outlet air temperature of approximately 41° C. with a range of 39.0–41.0° C. The inlet air temperature generally ranged from 55–62° C. and a supply air flow rate of 1700–1900 cubic feet per minute is used. The coating solution flow rate is started at approximately 250 g/min and increased periodically to reach a final spray rate of approximately 375–400 g/min. An atomizing air pressure of 60 psi is used during spraying of the coating solution. The total coating process time is 1.5 hours per coating sub-batch. Process time for 10 sub-batches is 15 hours.

TABLE 4

Pseudoephedrine HCl Wax Granulation Formulation Commercial Scale.

| Component | Quantity (mg/gm) | Quantity (kg/600 kg Batch Size) |
|---|---|---|
| Pseudoephedrine HCl | 281.7 | 169.0 |
| Carnauba Wax, NF | 704.3 | 422.6 |
| Stearic Acid Flakes, NF | 11.50 | 6.9 |
| Colloidal Silicon Dioxide, NF | 2.50 | 1.5 |

TABLE 5

Piperidinoalkanol[1] Final Blend Formulation Commercial Scale.

| Component | Quantity (mg/gm) | Quantity (kg/482.8 kg Blend Batch Size) |
|---|---|---|
| ***Piperidinoalkanol[1] Granulation | 438.6 | 211.8 |
| Microcrystalline Cellulose (Avicel PH 102) | 542.5 | 261.9 |
| Croscarmellose, Sodium | 11.40 | 5.504 |
| Magnesium Stearate | 7.5 | 3.621 |

***Piperidinoalkanol[1] Granulation

| Component | Quantity (mg/gm) | Quantity (kg/211.8 kg Granulation) |
|---|---|---|
| Piperidinoalkanol[1] Drug Substance | 389.6 | 82.52 |
| Croscarmellose, Sodium | 51.95 | 11.00 |
| Pregelatinized Starch | 389.6 | 82.52 |
| Microcrystalline Cellulose (Avicel PH 101) | 168.8 | 35.75 |
| Water, Purified USP[2] | 390.0 | 82.60 |

TABLE 5-continued

Piperidinoalkanol[1] Final Blend Formulation Commercial Scale.

[1]4-[4-[4-(Hydroxydiphenylmethyl)-1-piperdinyl]-1-hydroxybutyl]-α,α-dimethylbenzeneacetic acid hydrochloride.
[2]Water is removed during the process and does not appear in the final product. The amount of water may be varied to achieve suitable granulation.

Method for Determining Content Uniformity.

Content uniformity is determined by one of ordinary skill in the art utilizing known techniques and procedures. One of ordinary skill in the art for example, may utilize an isocratic HPLC procedure wherein an Alltech Adsorbosphere XL SCX, 5μm (50 mm×4.6 mm ID) strong base cation exchange column followed in series by a Zorbax SB-Phenyl, 5 μm (250 mm×4.6 mm ID) reverse phase column is employed. A mobile phase consisting of 65:35 v/v methanol:buffer (0.050 M sodium acetate and 0.075 M 1-octanesulfonic acid, sodium salt, pH=4.60 by adjusting with acetic acid) is pumped through the column at a flow rate of 1.5 mL/min. The column temperature is maintained at 35° C. Standards and samples are injected onto the column using a 20 μL injection volume followed by UV detection at 215 nm.

Ten individual tablet samples are prepared as follows. One tablet is placed into a 100-mL volumetric flask and 60.0 mL of methanol is added. The flask is stoppered and shaken for 60 minutes on a mechanical shaker set at high speed. After the shaking period, the flask is placed into an Ultrasonic-Heating Bath and sonicated at 40° C. for 60 minutes. During the 60 minute sonication period, the flask is vigorously shaken by hand every 15 minutes to help break up the tablets. After the initial 60 minute sonication period, 35 mL of the buffer (0.050 M sodium acetate and 0.075 M 1-octanesulfonic acid, sodium salt, pH=4.60 by adjusting with acetic acid) is added into the flask, mixed, then placed into an Ultrasonic-Heating Bath for a second time and sonicated at 40° C. for 60 minutes. During the second 60 minute sonication period, the flask is vigorously shaken by hand every 15 minutes to help break up the tablets. After the second sonication period the flasks are removed from the sonicator and allowed to cool to room temperature. After reaching room temperature, the flask is shaken/mixed, then the majority of the floating excipients are poured off into a waste container. Approximately 6–8 mL of the remaining sample solution is filtered into a small beaker using a 0.45 μm Whatman GD/X filter, yielding a Sample Solution I. Using a volumetric pipette, 4.0 mL of the Sample Solution I is pipetted into a 50-mL volumetric flask, diluted to volume with mobile phase yielding Sample Solution II, and injected into the HPLC system. Peak areas for pseudoephedrine and 4-[4-[4-(hydroxydiphenylmethyl)-1-piperdinyl]-1-hydroxybutyl]-α,α-dimethylbenzeneacetic acid are determined and the percent of label claim is calculated for each active.

TABLE 6

Uncoated Bilayer Tablet In-Process Content Uniformity; 4-[4-[4-(Hydroxydiphenylmethyl)-1-piperdinyl-1-hydroxybutyl]-α,α-dimethylbenzeneacetic acid Hydrochloride Content Uniformity, n = 10.

| Sampling Time During Compression | Mean % Label Claim | rsd | Range % Label Claim |
|---|---|---|---|
| Beginning | 100.6 | 2.0 | 98.1 to 103.1 |
| 1 hour | 101.5 | 3.5 | 95.5 to 106.0 |

TABLE 6-continued

Uncoated Bilayer Tablet In-Process Content Uniformity; 4-[4-[4-(Hydroxydiphenylmethyl)-1-piperdinyl-1-hydroxybutyl]-α, α-dimethylbenzeneacetic acid Hydrochloride Content Uniformity, n = 10.

| Sampling Time During Compression | Mean % Label Claim | rsd | Range % Label Claim |
|---|---|---|---|
| 3 hours | 100.1 | 2.5 | 96.2 to 103.2 |
| 4 hours | 100.0 | 3.2 | 96.5 to 105.2 |
| 5 hours/ending | 91.9 | 2.9 | 95.4 to 104.4 |

TABLE 7

Uncoated Bilayer Tablet In-Process Content Uniformity; Pseudoephedrine Hydrochloride Content Uniformity, n = 10.

| Sampling Time During Compression | Mean % Label Claim | rsd | Range % Label Claim |
|---|---|---|---|
| Start | 101.8 | 1.1 | 100.1 to 103.3 |
| 1 hour | 100.8 | 1.8 | 98.7 to 104.8 |
| 3 hours | 100.6 | 1.0 | 99.5 to 102.4 |
| 4 hours | 100.0 | 3.7 | 96.5 to 109.7 |
| 5 hours/ending | 102.0 | 1.1 | 100.5 to 104.6 |

Tables 6 and 7 provide the content uniformity for 4-[4-[4-(hydroxydiphenylmethyl)-1-piperdinyl]-1-hydroxybutyl]-α,α-dimethylbenzeneacetic acid hydrochloride and pseudoephedrine hydrochloride respectively. Good content uniformity ensures that every tablet contains the amount of drug substance intended with little variation among tablets within a batch. In order to establish good content uniformity, the United States Pharmacopeia 23, The United States Pharmacopeial Convention, Inc., Rockville, Md., page 1838, sets a deviation of less than or equal to 6% and all individual tablets must lie within 85.0% to 115.0% of label claim for a sample of 10 tablets. As revealed above, the present invention provides a pharmaceutical composition which exhibits good content uniformity wherein the largest variation observed for 4-[4-[4-(hydroxydiphenylmethyl)-1-piperdinyl]-1-hydroxybutyl]-α, α-dimethylbenzeneacetic acid hydrochloride was 3.5% RSD at the 1 hour sample and for pseudoephedrine hydrochloride was 3.7% RSD at the 3 hour sample.

Dissolution Method.

Dissolution profiles are determined by one of ordinary skill in the art utilizing known techniques and procedures. For example, dissolution testing is performed in 900 mL of 0.001 N HCl (pH=3.00) maintained at 37° C. using USP paddle (Apparatus 2, see for example Remington's Pharmaceutical Sciences, Mack Publishing Company, (1990), Eighteenth Edition, pages 595–596) method with a rotation speed of 50 RPM. Aliquots of each dissolution test solution are collected and filtered through 45 μm polyethylene sampling filters at the sampling intervals of 15, 30, 45, 60, 180, 300, 420, and 720 minutes. Each aliquot of the collected dissolution sample solution is analyzed using an isocratic HPLC procedure utilizing a Whatman Partisil 10 SCX (250 mm×4.6 mm ID) strong base cation exchange column. A mobile phase consisting of 45:55 v/v acetonitrile:buffer (0.05 M sodium phosphate, pH=2.00±0.05) is pumped through the column at a flow rate of 1.0 mL/min. The column temperature is maintained at ambient room temperature. Standards and samples are injected onto the column using a 10 μL injection volume followed by UV detection at 210 nm. Peak areas for pseudoephedrine and 4-[4-[4-(hydroxydiphenylmethyl)-1-piperdinyl]-1-hydroxybutyl]-α, α-dimethylbenzeneacetic acid are determined and the percent of label claim released at each time interval is calculated for each active.

TABLE 8

Uncoated Bilayer Tablet Dissolution Profile for 4-[4-[4-(Hydroxydiphenylmethyl)-1-piperdinyl]-1-hydroxybutyl]-α, α-dimethylbenzeneacetic acid Hydrochloride Dissolution.

| Sampling Time During Compression | 0.25 h Mean (rsd) | 0.5 h Mean (rsd) | 1.0 h Mean (rsd) |
|---|---|---|---|
| Start | 89.6 (3.7) | 95.9 (2.4) | 97.7 (2.6) |
| 1 hour | 88.2 (4.2) | 93.1 (3.7) | 96.0 (3.1) |
| 3 hours | 82.4 (9.1) | 88.0 (6.9) | 92.1 (4.9) |
| 4 hours | 96.3 (2.5) | 98.3 (2.4) | 99.2 (2.4) |
| 5 hours/end | 91.9 (3.6) | 94.9 (2.9) | 96.6 (2.2) |

TABLE 9

Uncoated Bilayer Tablet Dissolution Profile for Pseudoephedrine Hydrochloride.

| Sampling Time During Compression | 0.25 h Mean (rsd) | 0.5 h Mean (rsd) | 1 h Mean (rsd) | 3 h |
|---|---|---|---|---|
| Start | 20.9 (2.8) | 29.9 (1.6) | 41.4 (1.6) | 67.5 (1.8) |
| 1 hour | 21.0 (1.9) | 29.7 (2.2) | 41.5 (2.2) | 67.4 (1.5) |
| 3 hour | 20.9 (2.6) | 29.5 (1.0) | 41.2 (1.7) | 67.1 (1.0) |
| 4 hour | 21.0 (2.0) | 29.6 (1.5) | 41.3 (1.1) | 67.4 (1.2) |
| 5 hours/end | 21.4 (1.8) | 30.1 (1.5) | 41.7 (1.6) | 68.0 (1.9) |

| Sampling Time During Compression | 5 h Mean (rsd) | 7 h Mean (rsd) | 10 h Mean (rsd) | 12 h Mean (rsd) |
|---|---|---|---|---|
| Start | 81.2 (1.2) | 89.2 (1.0) | 93.8 (1.0) | 94.9 (1.2) |
| 1 hour | 80.3 (1.1) | 88.9 (1.2) | 93.7 (1.2) | 95.1 (1.1) |
| 3 hour | 80.3 (1.1) | 88.2 (1.2) | 93.0 (1.0) | 94.5 (0.9) |
| 4 hour | 80.6 (0.9) | 87.8 (0.9) | 92.8 (1.0) | 94.4 (0.9) |
| 5 hours/end | 81.3 (1.7) | 88.4 (1.6) | 93.7 (1.5) | 95.3 (1.5) |

TABLE 10

Dissolution of SUDAFED 12 HOUR ® Tablets; Percent of Label Claim Released

| Test Media | Percent Pseudoephedrine Dissolved (% of LC) | | | | | | | | |
|---|---|---|---|---|---|---|---|---|---|
| | .25 Hr | 0.5 Hr | 0.75 Hr | 1.0 Hr | 3.0 Hr | 5.0 Hr | 7.0 Hr | 10 Hr | 12 Hr |
| 1 mm HCl | 14.5 | 25.9 | 34.5 | 41.3 | 71.8 | 87.2 | 95.7 | N/A | 101.1 |

TABLE 11

| Dissolution of ALLEGRA ® capsules in 1 mm HCl Media; Percent of Label Claim Released. | | | |
|---|---|---|---|
| 0.25 Hr | 0.50 Hr | 0.75 Hr | 1.0 Hr |
| 81.1% | 87.5% | 90.7% | 92.8% |

Tables 8 and 9 provide the dissolution profiles for 4-[4-[4-(hydroxydiphenylmethyl)-1-piperdinyl]-1-hydroxybutyl]-α,α-dimethylbenzeneacetic acid hydrochloride and pseudoephedrine hydrochloride respectively. Tables 10 and 11 provide the dissolution profiles for SUDAFED 12 HOUR® Tablets and ALLEGRA® capsules respectively.

What is claimed is:

1. A pharmaceutical composition in the form of a bilayer tablet comprising,
   (a) a first discrete zone made with Formulation (A) which comprises, a therapeutically effective decongestant amount of a sympathomimetic drug, or a pharmaceutically acceptable salt thereof, in an amount of about 18% to about 39% by weight of Formulation (A), and a first carrier base material, the first carrier base material comprising a mixture of;
      (I) carnauba wax in an amount of about 59% to about 81% by weight of Formulation (A); and
      (ii) a suitable antiadherent in an amount of about 0.25% to about 2.00% by weight of Formulation (A);
   wherein said first carrier base material provides a sustained release of the sympathomimetic drug; and
   (b) a second discrete zone made with Formulation (B) which comprises a therapeutically effective antihistaminic amount of a piperidinoalkanol, or a pharmaceutically acceptable salt thereof, in an amount of about 15% to about 30% by weight of Formulation (B) and a second carrier base material, the second carrier base comprising a mixture of;
      (I) a cellulose diluent in an amount of about 27% to about 73% by weight of Formulation (B);
      (ii) pregelatinized starch in an amount of about 15% to about 30% by weight of Formulation (B);
      (iii) a suitable disintegrant in an amount of about 0.25% to about 6.00% by weight of Formulation (B); and
      (iv) a suitable lubricant in an amount of about 0.25% to about 2.00% by weight of Formulation (B);
   wherein said second carrier base material provides an immediate release of the piperidinoalkanol or the pharmaceutically acceptable salt thereof.

2. The pharmaceutical composition of claim 1 wherein the piperidinoalkanol is of the formula;

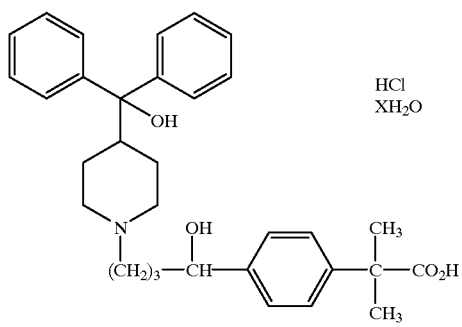

wherein X is a number ranging from about zero to about 5, and the individual optical isomers thereof.

3. A pharmaceutical composition in the form of a bilayer tablet comprising,
   (a) a first discrete zone made with Formulation (A) which comprises, a therapeutically effective decongestant amount of a sympathomimetic drug, or a pharmaceutically acceptable salt thereof in an amount of about 25% to about 33% by weight of Formulation (A), and a first carrier base material, the first carrier base material comprising a mixture of;
      (I) carnauba wax in an amount of about 66% to about 74% by weight of Formulation (A); and
      (ii) a suitable antiadherent in an amount of about 0.50% to about 1.50% by weight of Formulation (A);
   wherein said first carrier base material provides a sustained release of the sympathomimetic drug; and
   (b) a second discrete zone made with Formulation (B) which comprises a therapeutically effective antihistaminic amount of a piperidinoalkanol of the formula;

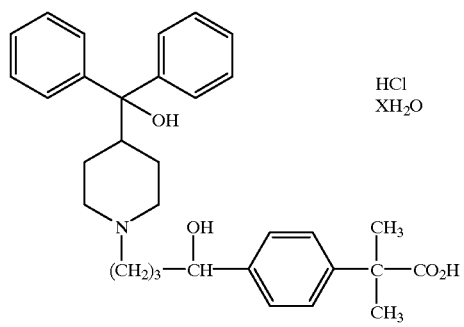

wherein X is a number ranging from about zero to about 5, and the individual optical isomers thereof, in an amount of about 15% to about 24% by weight of Formulation (B) and a second carrier base material, the second carrier base comprising a mixture of;
      (I) a cellulose diluent in an amount of about 43% to about 67% by weight of Formulation (B);
      (ii) pregelatinized starch in an amount of about 15% to about 24% by weight of Formulation (B);
      (iii) a suitable disintegrant in an amount of about 3.20% to about 4.80% by weight of Formulation (B); and
      (iv) a suitable lubricant in an amount of about 0.50% to about 1.00% by weight of Formulation (B);
   wherein said second carrier base material provides an immediate release of the piperidinoalkanol or the pharmaceutically acceptable salt thereof.

4. A pharmaceutical composition according to claim 1 wherein a suitable glidant is included in the first carrier base material of Formulation (A) in an amount of 0.00% to about 3.00% by weight of Formulation (A).

5. A pharmaceutical composition according to claim 1 wherein a suitable glidant is included in the first carrier base material of Formulation (A) in an amount of 0.00% to about 0.75% by weight of Formulation (A).

6. A pharmaceutical composition according to claim 5 wherein the suitable glidant is colloidal silicon dioxide.

7. A pharmaceutical composition according to either claim 3 or claim 6 wherein the sympathomimetic drug is pseudoephedrine hydrochloride.

8. A pharmaceutical composition according to claim 7 wherein the suitable antiadherent of Formulation (A) is stearic acid, and in Formulation (B), the suitable disintegrant is croscarmellose sodium and the suitable lubricant is magnesium stearate.

9. A pharmaceutical composition according to claim 8 wherein the pseudoephedrine hydrochloride, carnauba wax, stearic acid and colloidal silicon dioxide of Formulation (A) are combined in amounts of about 28.17%, about 70.42%, about 1.15% and about 0.25% respectively, by weight of the composition of Formulation (A), and the piperidinoalkanol, cellulose diluent, pregelatinized starch, croscarmellose sodium and magnesium stearate of Formulation (B) are combined in amounts of about 17.09%, about 61.67%, about 17.09%, about 3.42% and about 0.75% respectively, by weight of the composition of Formulation (B).

10. The pharmaceutical composition according to claim 9 wherein the piperidinoalkanol is 4-[4-[4-(hydroxydiphenylmethyl)-1-piperdinyl]-1-hydroxybutyl]-α,α-dimethylbenzeneacetic acid hydrochloride.

11. The pharmaceutical composition according to claim 10 wherein the 4-[4-[4-(hydroxydiphenylmethyl)-1-piperidinyl]-1-hydroxybutyl-α,α-dimethylbenzeneacetic acid hydrochloride is present in an amount of about 60 mg and the pseudoephedrine hydrochloride is present in an amount of about 120 mg.

12. A pharmaceutical composition according to claim 11 wherein the bilayer tablet is coated with a suitable coating agent.

13. A pharmaceutical composition according to claim 11 wherein the bilayer tablet has a hardness of about 15 kp to about 25 kp.

* * * * *

UNITED STATES PATENT AND TRADEMARK OFFICE
CERTIFICATE OF CORRECTION

PATENT NO. : 6,039,974

DATED : March 21, 2000

INVENTOR(s) : David D. MacLaren, John R. Lefler, Sharon K. Minish

It is certified that error appears in the above-identified patent and that said Letters Patent is hereby corrected as shown below:

Column 10, line 45, after "range" delete --IS--;

Column 12, line 35, change "µ" to --µg--; and

Column 13, line 18, after "-α" insert --,α-dimethylbenzeneacetic acid hydrocholoride--.

Signed and Sealed this

Fifteenth Day of May, 2001

*Attest:*

NICHOLAS P. GODICI

*Attesting Officer*    Acting Director of the United States Patent and Trademark Office